United States Patent [19]
Greenberg

[11] Patent Number: 5,558,622
[45] Date of Patent: Sep. 24, 1996

[54] MANDIBULAR BORDER RETRACTOR AND METHOD FOR FIXATING A FRACTURED MANDIBLE

[75] Inventor: Alex M. Greenberg, New York, N.Y.

[73] Assignee: Greenberg Surgical Technologies, LLC, New York, N.Y.

[21] Appl. No.: 300,708

[22] Filed: Sep. 2, 1994

[51] Int. Cl.⁶ .................................................. A61C 11/00
[52] U.S. Cl. .................... 600/237; 600/210; 600/235; 600/238; 600/190
[58] Field of Search .................... 600/201, 210, 600/217, 235, 237, 238, 239, 240, 241, 242, 245, 190; 433/93, 94, 140

[56] References Cited

U.S. PATENT DOCUMENTS

| | | | |
|---|---|---|---|
| 2,831,480 | 4/1958 | Milano | 433/93 X |
| 2,840,070 | 6/1958 | Tofflemire | 600/237 X |
| 3,090,122 | 5/1963 | Erickson | 600/238 X |
| 4,971,557 | 11/1990 | Martin | 433/140 |
| 5,035,232 | 7/1991 | Lutze et al. | 600/245 X |

FOREIGN PATENT DOCUMENTS

| | | | |
|---|---|---|---|
| 2133694 | 8/1984 | Germany | 600/245 |

OTHER PUBLICATIONS

Walter Lorenz Surgical Instruments, Inc. Catalog, pp. 213, 245, 250, 252–57, 259–61, and 263 (1993).

Primary Examiner—Richard J. Apley
Assistant Examiner—Beverly M. Flanagan
Attorney, Agent, or Firm—Meltzer, Lippe, Goldstein, et al.

[57] ABSTRACT

A mandibular retractor which is inserted intraorally has a retractor blade shaped to retract the cutaneous region laterally away from the mandible. The retracting blade also has an aperture which allows surgical instruments to be inserted through an incision in the cutaneous region, through the aperture, and to the mandible. The retractor allows a surgeon to retract with one hand and view the surgical site by looking down in to the mouth. The surgeon's other hand is free to operate surgical instruments such as a drill or screwdriver.

39 Claims, 15 Drawing Sheets

5,558,622

1

MANDIBULAR BORDER RETRACTOR AND METHOD FOR FIXATING A FRACTURED MANDIBLE

FIELD OF THE INVENTION

The present invention relates to a mandibular retractor and method for fixating a fractured mandible. More particularly, the invention relates to a mandibular retractor and fixation method which improves the surgeon's access and visibility of the surgical site and which allows a surgeon to fixate a fractured mandible, reducing or eliminating the need for a surgical assistant.

BACKGROUND OF THE INVENTION

The treatment of bone fractures in craniomaxillofacial regions generally proceeds by reducing the fractured bone to its anatomically correct position, and thereafter fixing the bone in place. This procedure is known as an open reduction/internal fixation or "ORIF". In an ORIF, the bone may be fixed in place either by interosseous wiring or by the technique of miniplate (or bone plate) osteosynthesis. See Greenberg, A. M., editor *Craniomaxillofacial Fractures: Principles of Internal Fixation Using the AO/ASIS Technique,* Springer Verlag, New York (1993). In either case, holes must be drilled into the bone for receiving the interosseous wire or screws for holding the bone plates to the bone.

FIG. 1 shows a fractured mandible. The mandible M has a fracture F. The patient's skin S is shown in cutaway view. The mandibular nerve N runs through the mandible M and exits into the skin S at an anterior portion of the mandible, where it becomes the mental nerve ME, which is a delicate structure. The fractured mandible is treated with an ORIF procedure. The present invention is explained with respect to bone plate osteosynthesis, but a person skilled in the art will readily understand that the disclosure is equally applicable to interosseous wiring.

FIGS. 2 and 2A show a greatly enlarged bone plate P useful in the treatment of mandibular fractures. Numerous different configurations of the bone plate may be used depending on the size and shape of the fracture and bone structure to be reduced. The bone plate P is just one example of a suitable bone plate. The bone plate P consists of a chain-like body 41 having holes 42 therein. Each of the holes 42 is countersunk with a beveled edge 43 so that the holes 42 are adapted to receive surgical screws (not shown) and to retain the reduced bone in place until the bone heals. The bone plate holds the bone structure together so that it can heal.

An exemplary prior art intraoral (i.e., through the mouth) mandibular ORIF procedure is described as follows. As shown in FIG. 3A, a mandible M has a fracture F. The patient's skin S and tongue T are also shown. An incision SI is made through the patient's cutaneous region near the fracture F. A second incision, referred to here as the oral incision OI, is made in the buccal vestibule. The oral incision OI is generally V-shaped and runs parallel to the mandible M, as shown in FIG. 3B. Care is taken to locate and preserve the mental nerve. The, presence of the mental nerve at the anterior portion of the mandible M confines the area that the surgeon can access. Thus, the surgeon is confined to a small space in which to operate and accommodate surgical instruments.

2

As shown in FIG. 3A, two right angle retractors LR retract the mouth so that the fracture may be viewed. As seen in FIG. 3C, the retractors LR pull the oral incision OI anteriorly and posteriorly (indicated by the opposing horizontal arrows on the retractors LR), causing tension in the V-shaped oral incision which tends to pull the lateral aspects towards each other (indicated by the vertical arrows), thus tending to limit the surgeon's access to the incision.

The mandible is reduced to its anatomically correct position. This typically requires a retractor to access the fracture F. After the mandible is successfully reduced, the bone should be fixed in its proper position to heal. This is typically done with either interosseous wiring or bone plate osteosynthesis. This requires drilling holes in the mandible. This typically requires (1) retracting the tissue from the mandible to view the surgical area; (2) holding a bone plate in position across the fracture; (3) holding a drill depth guide to prevent drilling too deeply, or through, the mandible; and (4) operating the drill.

FIG. 3D illustrates how a conventional intraoral mandibular fixation is performed using the miniplate osteosynthesis technique. A trocar or cannula T is inserted into the incision SI. A bone plate P is positioned across the fracture, typically by one of (1) a surgical assistant who introduces the plate P through the patient's mouth and holds the plate in position with a surgical instrument such as a clamp; (2) holding the plate in place on the tissue below; or (3) sitting the plate on the retractor's base. The surgeon then inserts a drill through the trocar T in incisions SI, OI into alignment with a hole in the bone plate P. Once aligned, the surgeon drills a hole into the bone and then screws a screw into the hole in the bone plate P, thus, affixing the bone plate P to the mandible M. Alternatively, a threaded opening may be tapped in the bone prior to the introduction of the screw. In such a case, a tap is applied to the hole drilled into the bone before the screw is applied. At least one screw is placed on each side of the fracture in order to stabilize the bone. No retractor is located behind the mandible during the fixation.

This procedure requires three or more "hands" to perform; that is, two hands are needed to retract the mouth. The surgeon's hands are occupied with the trocar T and the drill, tap, or screwdriver. Additional hands may be needed to hold the plate P in position. This is disadvantageous for several reasons. First, the anterior and posterior retraction limits the surgeon's access to the oral incision, limiting the surgeon's view of and access to the surgical site. Second, the more "hands", instruments, or other obstructions in the area of the surgical site (here, at least two hands are needed to hold the retractors) reduces the surgeon's already limited visibility of the surgical site. There is the additional expense of a surgical assistant. Surgical assistants are relatively costly to the patient. Many insurance companies are searching for ways to reduce the expense of surgical assistants and some have eliminated insurance payments for the assistant altogether for certain procedures, leaving the expense of the assistant on the patient.

The prior art retractors and surgical methods, while useful, are not entirely satisfactory for the procedure described above.

Accordingly, it is an object of the present invention to provide a mandibular border retractor which reduces or eliminates the role of a surgical assistant in mandibular ORIF procedures.

A further object of the invention is to provide a retractor which improves the ease of an intraoral fracture reduction, thus reducing the likelihood of the patient undergoing an extraoral (transcutaneous) approach. The extraoral approach requires longer operating and hospitalization times and increases the likelihood of complications.

It is a further object of the present invention to provide a retractor that allows the surgeon to reduce the mandible, retract and view the surgical site, and hold the bone plate in position with a single hand, leaving the other hand free to operate surgical instruments.

It is yet a further object of the invention to provide a retractor which retracts the lateral aspect of an oral incision, thereby not placing tension on the incision which would limit the surgeon's access to surgical site.

It is yet another object of the present invention to provide a mandible retractor having an aperture through which retracts of the lateral aspect of the oral incision and also permits a drill guide, drill, or other surgical instrument to access the surgical site.

It is yet a further object of the present invention to provide a retractor which includes an integral surgical instrument holder.

It is yet a further object of the present invention to provide a clamp for grasping or reducing a mandible.

SUMMARY OF THE INVENTION

These and other objects of the invention are achieved by the present invention. The present invention is a mandibular retractor which is inserted into the patient's mouth and has a curvilinearly-shaped retractor blade to retract the cutaneous region away from the mandible laterally. The retracting blade has an aperture which allows surgical instruments to be inserted through an incision in the cutaneous region, through the aperture, and to the mandible. The retractor also has an arcuate distal portion which may be located under and behind the mandible. The retractor allows a surgeon to retract with one hand and view the surgical site by looking down in to the mouth. The surgeon's other hand is free to operate surgical instruments such as a drill or screwdriver. No additional retractors are necessary, reducing the number of hands in the area of the surgery. The surgical assistant's role is reduced or eliminated.

The retractor may also include a shelf on the retracting blade below the aperture to hold a bone plate. This shelf acts as a carrier so that the bone plate may be positioned across the fracture when the retractor is inserted into the mouth and the tip is located behind the mandible.

The retractor may optionally include tapered side flanges to retract tissue away from a lateral end of the oral incision. The retractor may also optionally include a stabilizing arm which is located outside of the patient's mouth during the operation. The stabilizing arm may have an aperture aligned with the retractor blade aperture to permit surgical instruments to be inserted. The stabilizing arm may also include an adjustable surgical instrument retaining screw for holding surgical instruments in position. The retractor may also optionally include a moveable surgical instrument guide in the retractor blade aperture for holding surgical instruments in position.

The retractor according to the present invention may also be configured as a clamp which may, for example, be used to remove bone fragments. The retractor may also be configured as a reduction clamp which applies pressure on an opposite side of the mandible to reduce the fracture or to firmly hold a bone plate in place.

BRIEF DESCRIPTION OF THE DRAWINGS

These and other objects and features of the invention will become apparent from the following drawings, wherein.

DETAILED DESCRIPTION OF THE PREFERRED EMBODIMENTS OF THE INVENTION

Figure 1:
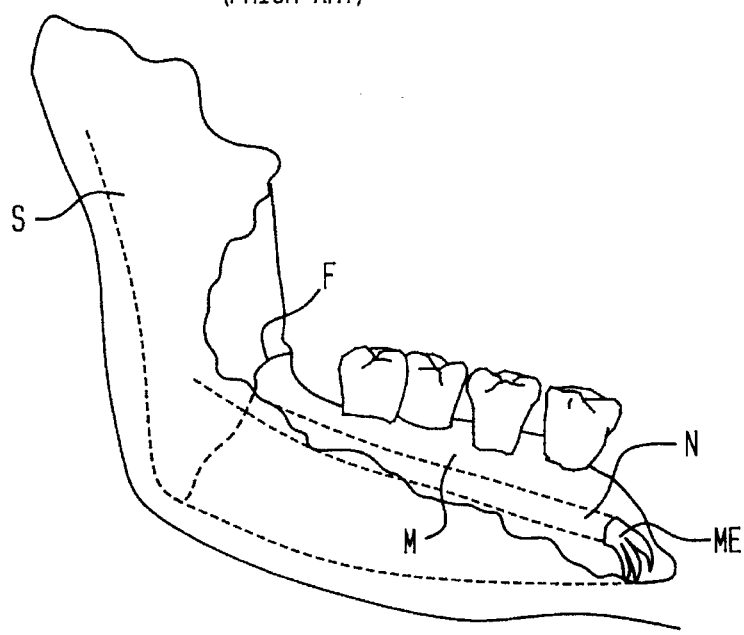
FIG. 1 illustrates a fractured mandible.
Figure 2:
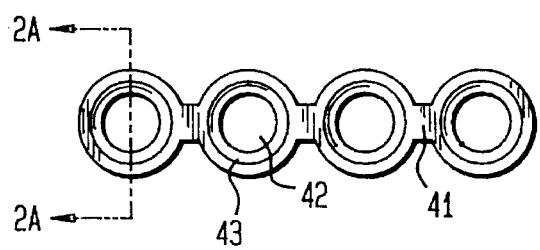
FIG. 2 illustrates a prior art bone plate for use in securing bone fragments together.
Figure 2A:
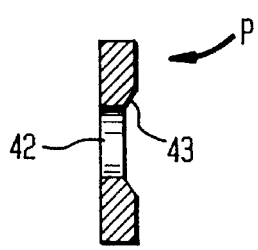
FIG. 2A is a cross sectional view of the bone plate of FIG. 2.
Figure 3A:
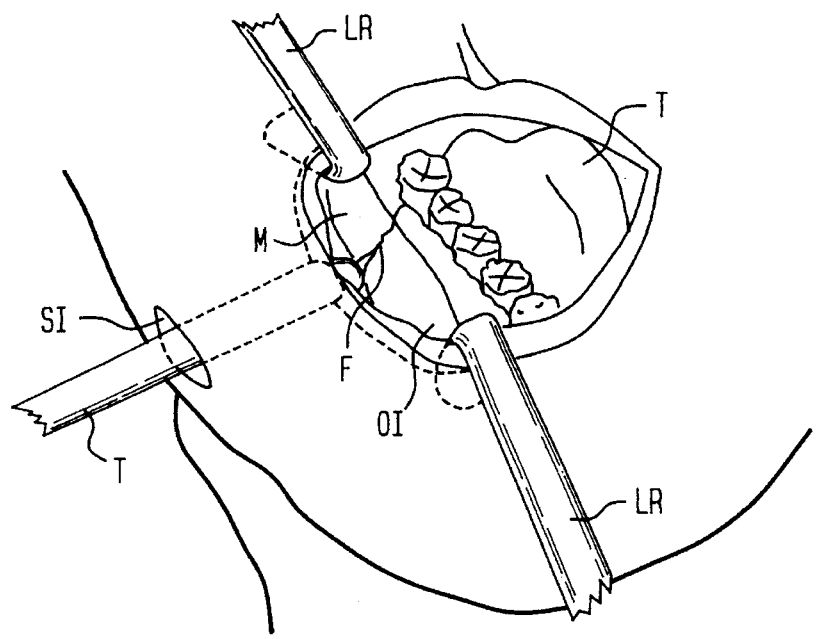
FIGS. 3A–3D illustrate a prior art intraoral ORIF procedure for the fractured mandible of FIG. 1.
Figure 3B:
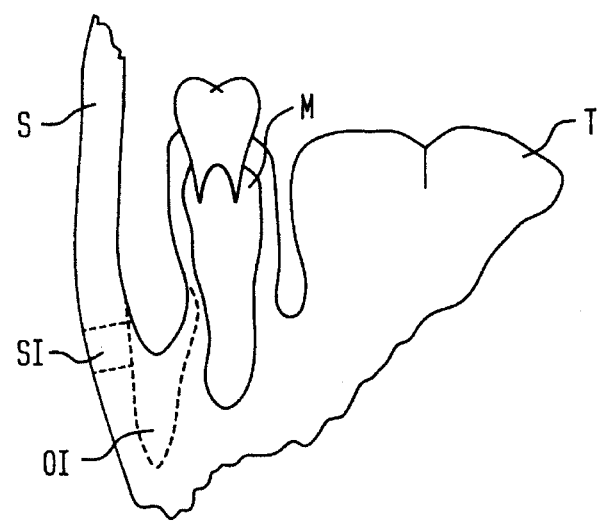
Figure 3C:
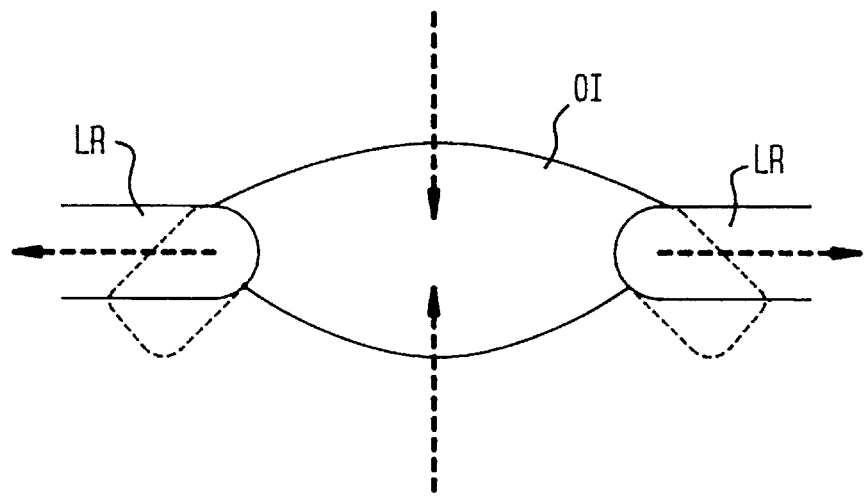
Figure 3D:
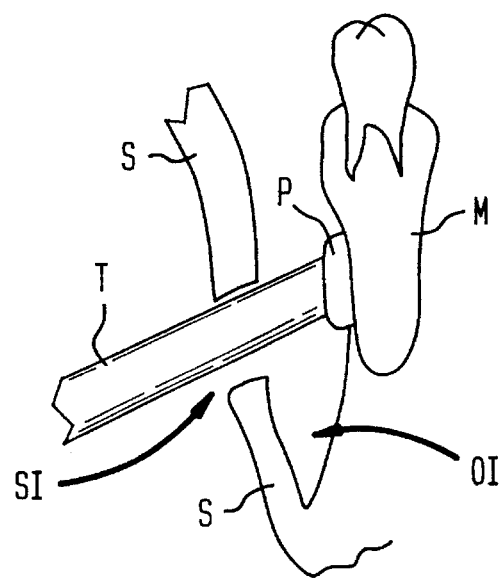
Figure 4:
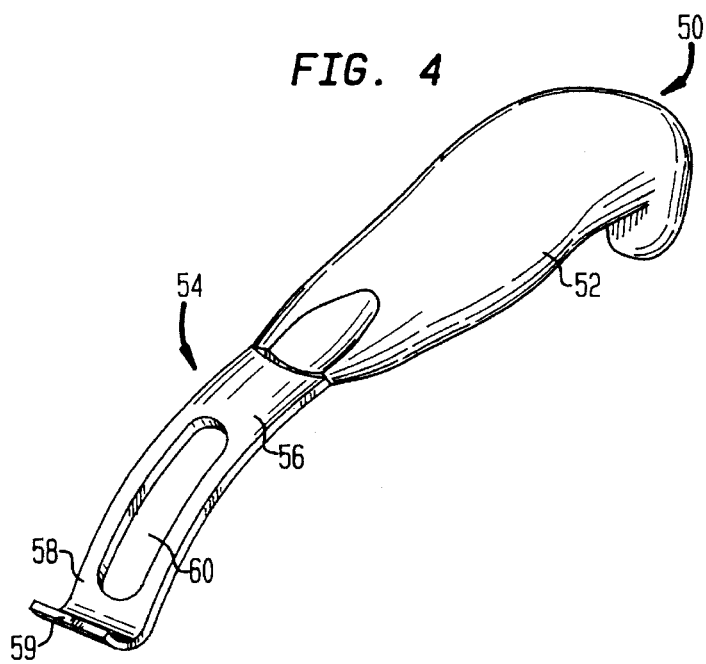
FIG. 4 is a perspective view of one embodiment of the retractor according to the invention.
Figure 5:
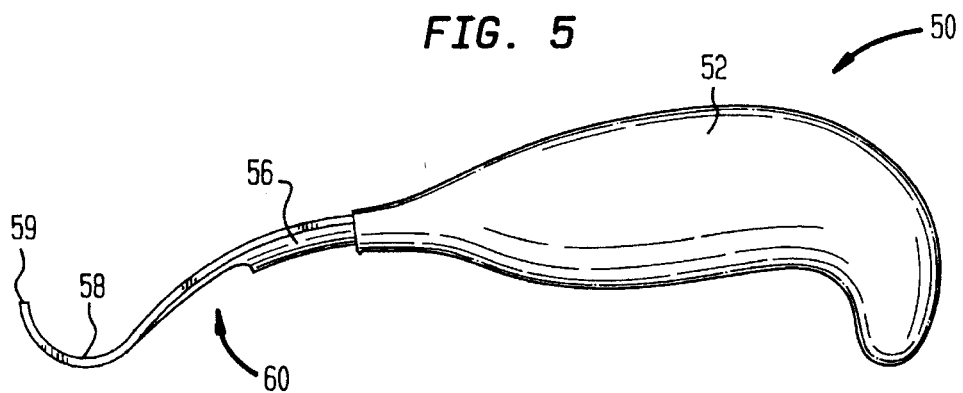
FIG. 5 is a side elevational view of the retractor of FIG. 4.
Figure 6:
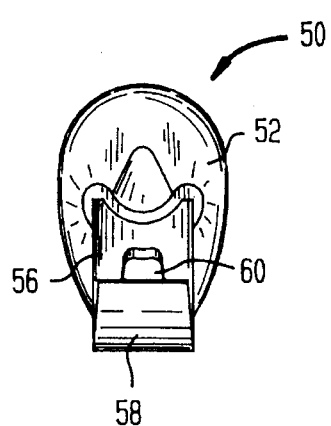
FIG. 6 is a front view of the retractor of FIG. 4.
Figure 7:
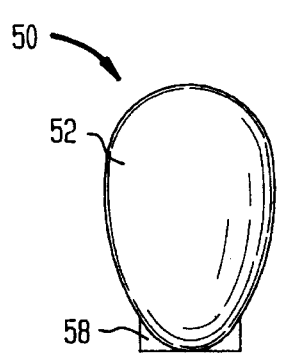
FIG. 7 is a back view of the retractor of FIG. 4.
Figure 8:
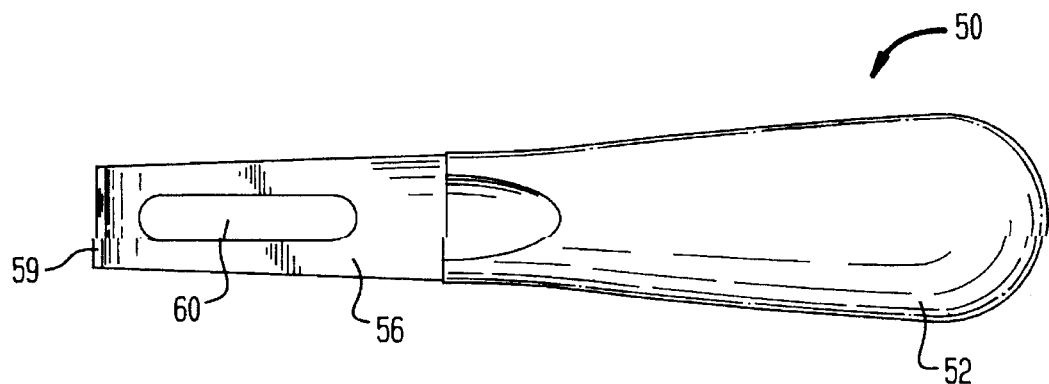
FIG. 8 is a top view of the retractor of FIG. 4.
Figure 9:
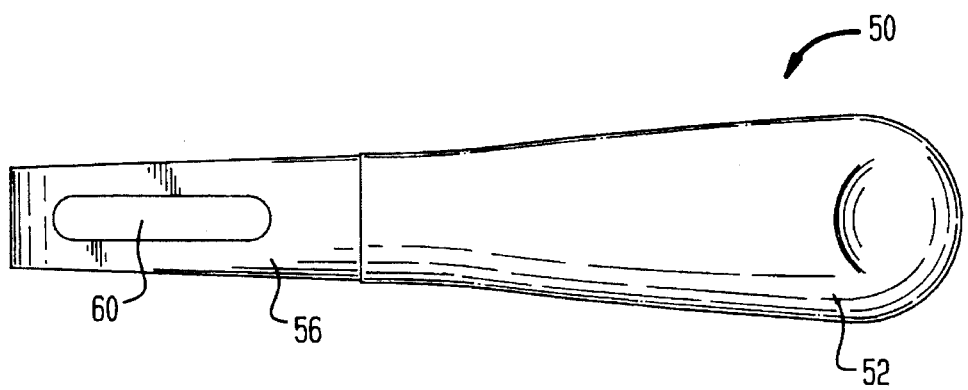
FIG. 9 is a bottom view of the retractor of FIG. 4.
Figure 10:
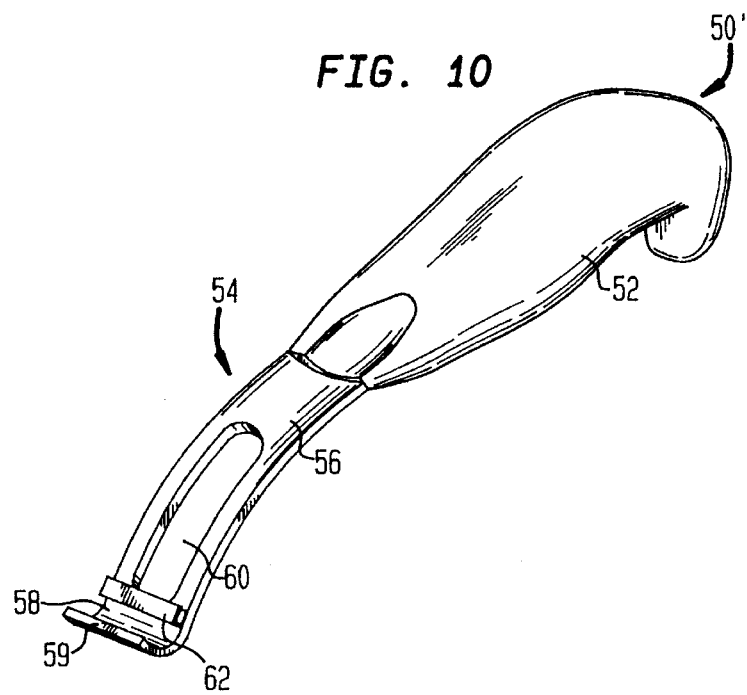
FIG. 10 is a perspective view of another embodiment of the retractor according to the invention.
Figure 11:
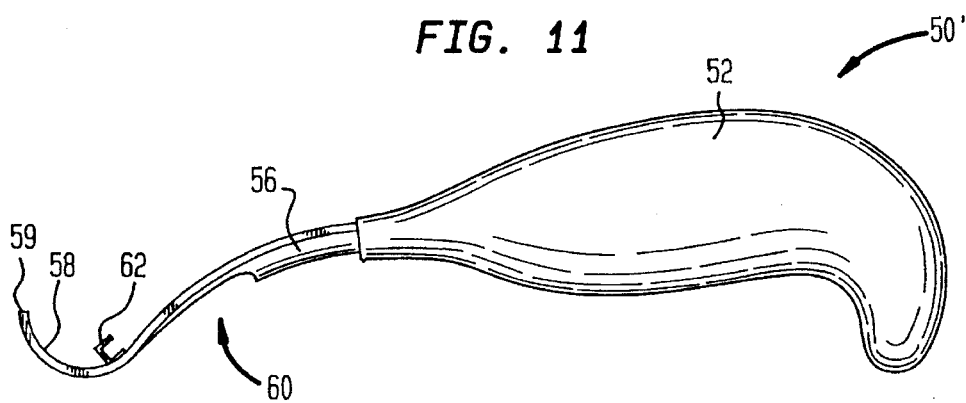
FIG. 11 is a side elevational view of the retractor of FIG. 10.
Figure 12:
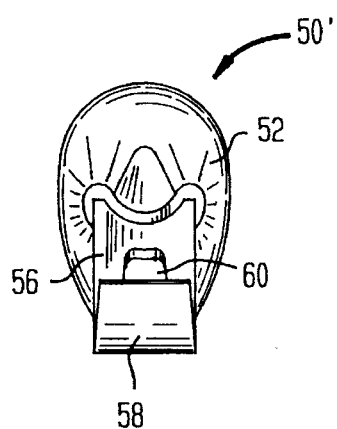
FIG. 12 is a front view of the retractor of FIG. 10.
Figure 13:
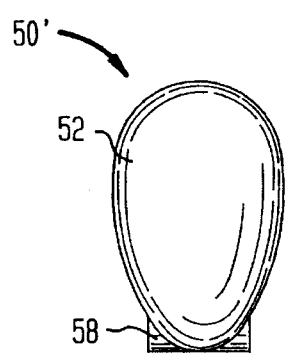
FIG. 13 is a back view of the retractor of FIG. 10.
Figure 14:
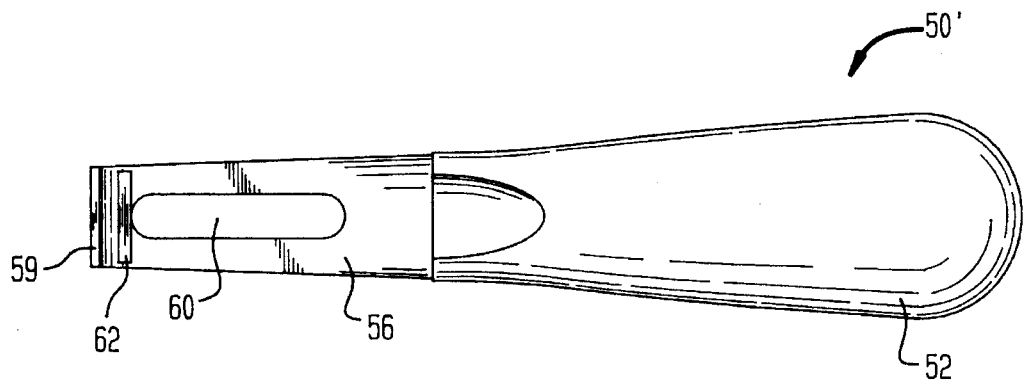
FIG. 14 is a top view of the retractor of FIG. 10.
Figure 15:
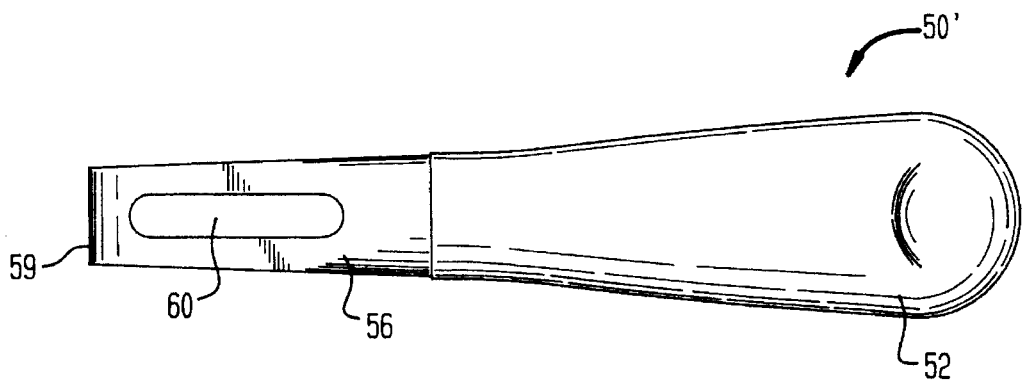
FIG. 15 is a bottom view of the retractor of FIG. 10.

A mandibular retractor 50 according to one embodiment of the present invention is shown in FIGS. 4–9. A handle 52 is located at the proximal end of the retractor 50. A retracting blade 54 is connected to the distal end of the handle 52. The retracting blade 54 comprises a curved portion 56 at the proximal end of the retractor blade 54, an arcuate portion 58 having a tip 59 at the distal end of the retractor blade 54, and an aperture 60 defined in the retracting blade 54 located proximally from the tip 59.

The curvature of the retracting blade according to the present invention is designed to be inserted into the patient's mouth and to hold the reduced mandible in place and retract the surgical site. The curved portion 56 has a long, gradual curvilinear shape. This curvature pulls the cheek in a direction away from the mandible sufficiently to allow observation of the surgical site. This shape allows retraction of the lateral aspect of the V-shaped oral incision, that is, in a direction generally perpendicular to the mandible. Retracting in this direction opens the V-shaped oral incision OI (see the arrow in FIG. 17.) The arcuate tip 58 is generally semi-circular and is designed to fit under and behind the mandible. Preferably, the tip does not extend too far upwards, because it may be impeded by soft tissue.

Figure 16:
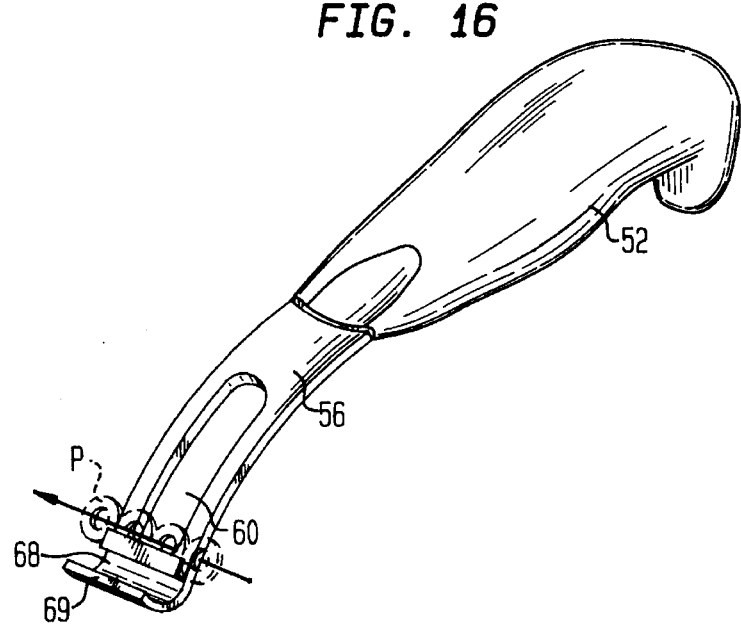
FIG. 16 is a perspective view of the retractor of FIG. 10 with a bone plate inserted on the shelf.

Another embodiment of the present invention is shown in FIGS. 10–16. A mandibular retractor 50' comprises a handle 52 and a retracting blade 54. In this embodiment, the retracting blade comprises a curved portion 56, an arcuate tip 58, an aperture 60 located proximally from the tip 58, and a shelf 64 located distally of the aperture 60. The shelf 64 is shaped to conform snugly to a bone plate P. As shown in FIG. 16, a bone plate P may be inserted into the shelf 64 before the retractor is placed in the patient's mouth. Thus, the shelf 64 operates as a carrier to locate the plate P at the fracture and hold it in place when the retractor 50' is positioned with respect to the mandible. The position of the shelf 64 between the tip 58 and the aperture 60 allows the bone plate holes 32 to align with the aperture 60. Thus, a straight line exists from the skin incision, through the retractor aperture 60 and the bone plate hole 32 to the mandible, as indicated by the arrow in FIG. 16. Also, there is no need for additional assistants or surgical instruments to position or hold the plate against the mandible.

Figure 17:
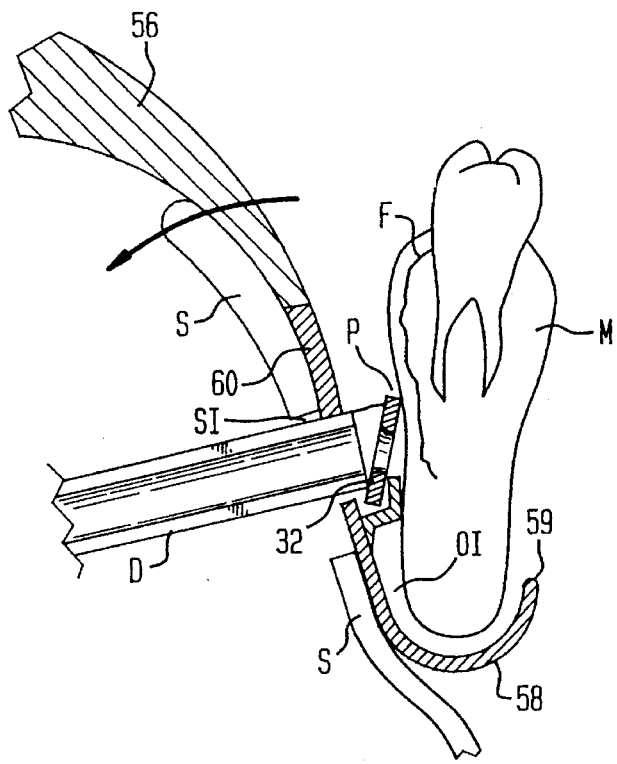
FIG. 17 illustrates a cross sectional view of the proximal end of the retractor of FIG. 10 used during a fixation of a fractured mandible.

The mandibular retractor according to the present invention is used as illustrated in FIG. 17 and described as follows. A skin incision SI and a V-shaped oral incision OI are made in the region of the fracture F. If the fracture is located anterior to the mental nerve, there may be no need for the skin incision and the procedure may be performed completely intraorally. If, as illustrated in FIG. 17, the fracture is posterior to or in the region of the mental nerve, a skin incision may be necessary. The retractor 50 is inserted into the patient's mouth and the arcuate portion 58 and tip 59 are manipulated through the oral incision OI to be positioned under and behind the fractured mandible M. The retractor is positioned so that the aperture 60 is aligned with the skin incision SI. The retractor is used to reduce the mandible M to its correct anatomical position. The patient's cutaneous region (skin S) may be retracted away from the mandible M in the direction of the arrow so that the surgeon may observe the surgical site by looking down into the patient's mouth. This retractor pulls the oral incision laterally, thus opening the oral incision OI, providing good visibility of the surgical site.

The surgeon places a bone plate P into position across the fracture. This may be done in the conventional fashion by having an assistant hold it in position, having the tissue support it, or having it sit on the retractor's base. Alternatively, the shelf 64 may be used. The surgeon's free hand may be used to operate a drill guide D, drill, screwdriver, or other surgical instrument. As is seen in FIG. 17, the aperture 60 allows the surgical instrument (e.g., the drill guide D) to extend through the retracting blade 54 to contact the bone plate P. A drill or other surgical instrument may then be used to drill a hole, tap a thread, screw in a screw, or otherwise access the mandible M.

Figure 18:
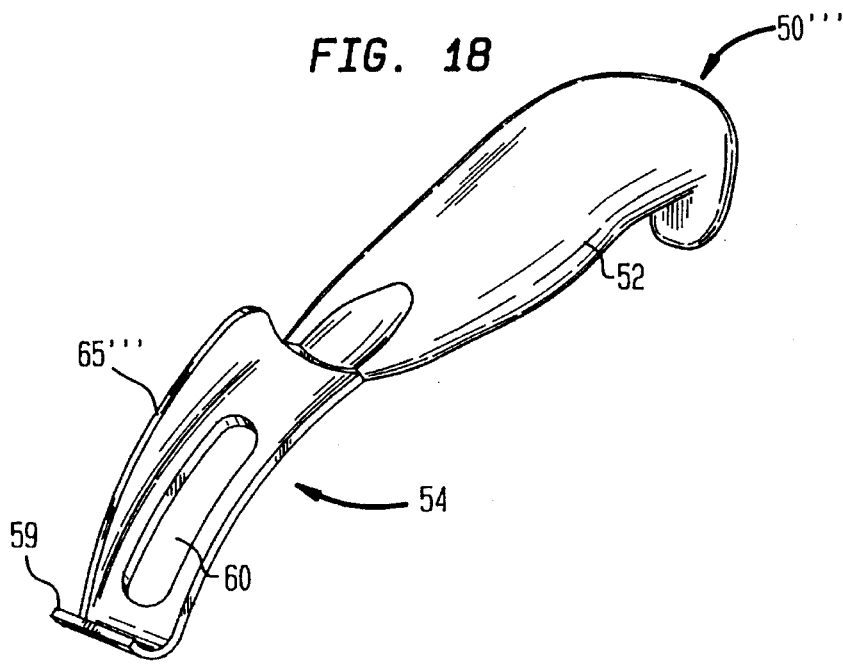
FIG. 18 is a perspective view of another embodiment of a retractor according to the present invention.
Figure 18A:
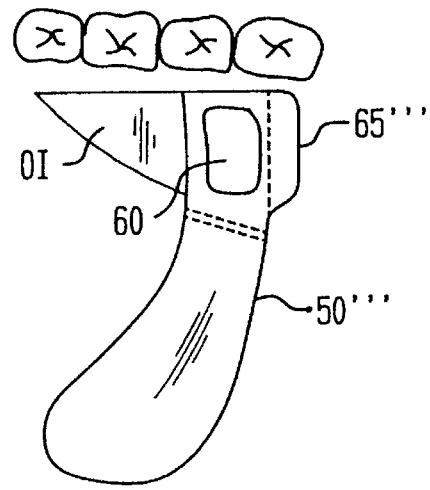
FIG. 18A illustrates a top view of the retractor of FIG. 18 inserted in an oral incision.
Figure 19:
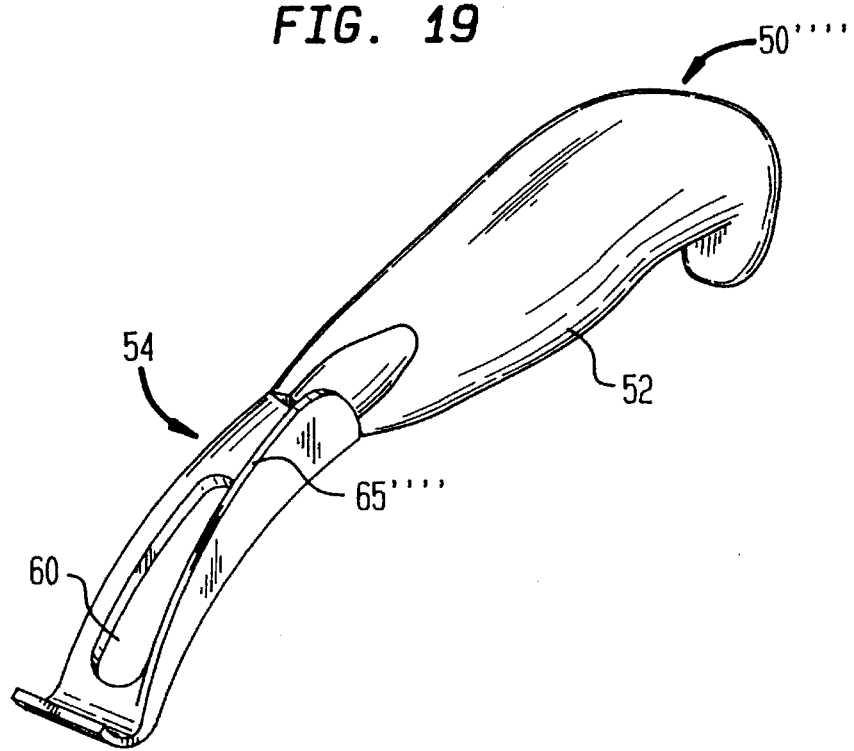
FIG. 19 is a perspective view of another embodiment of a retractor according to the present invention.

FIGS. 18 and 19 show further embodiments of the present invention. Retractors 50''' and 50'''' are substantially the same as the retractor illustrated in FIGS. 4–9, except for the addition of FLANGES 65''' and 65''''. A retractor having FLANGES 65''', 65'''' is used to further retract one side of the oral incision OI, preferably the anterior portions, thus further opening the site. As seen in FIG. 18A, the flange 65''' further opens oral incision OI. When the flange is used to retract the anterior portion of the oral incision OI, the wing also protects the mental nerve, which exits at an anterior portion of the mandible. The flanges 65''', 65'''' are preferably tapered for a wide portion near a proximal end of the retracting blade 54 to a narrow portion near a distal end of the retracting blade 54. This taper permits the flanges to get close to the mandible M.

Figure 20:
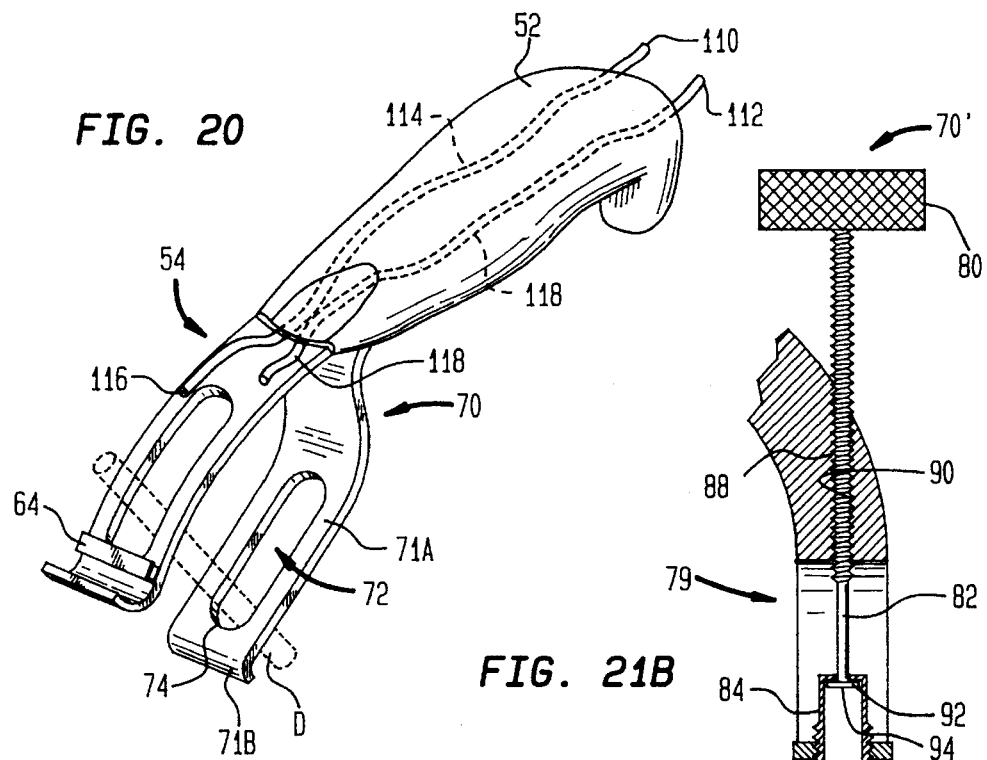
FIG. 20 is a perspective view of another embodiment of the retractor according to the present invention.

FIG. 20 illustrates another embodiment of a mandible retractor 50''''' according to the present invention. The mandible retractor 50''''' comprises a handle 52, a retracting blade 54, and a stabilizing arm 70. The stabilizing arm 70 initially extends in a direction generally perpendicular (preferably extending out at an angle between 30 and 100 degrees) to the retracting arm 54, to form roughly an inverted Y shape. The stabilizing arm 70 has a central portion 71 A which is generally parallel to the retracting blade 54 and a curved tip 71 B which curves in a direction opposite the arcuate portion tip 59 of the retractor blade. The stabilizing arm 70 includes a stabilizing arm aperture 72.

In use, the stabilizing arm 70 is located outside the patient's mouth and the stabilizing arm aperture 72 is aligned with the retracting blade aperture 60. The stabilizing arm aperture 72 stabilizes a surgical instrument, such as a drill guide D (shown in broken lines in FIG. 20). The instrument is stabilized by a bottom portion 74 of the stabilizing arm aperture 72. The instrument then extends through an incision in the patient's cutaneous region before extending through the aperture 60 in the retracting blade to contact a bone plate or the mandible.

Figure 21A:
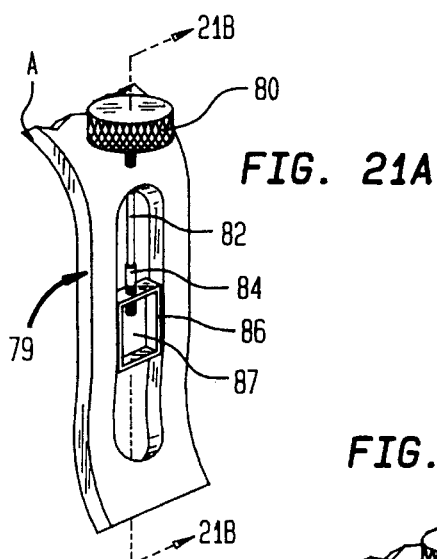
FIG. 21A is an exploded view of an alternative embodiment of the retractor of FIG. 20 having a surgical instrument retaining screw.
Figure 21B:
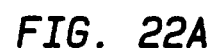
FIG. 21B is a cross sectional view of the embodiment of FIG. 21A.

FIGS. 21A and 21B illustrate another embodiment of the mandibular retractor of FIG. 20. This embodiment includes a stabilizing arm 70' which further includes a retaining screw mechanism 79 for retaining a surgical instrument, such as a drill guide, to be inserted through the apertures 72, 60. The retaining screw mechanism 79 includes a knob 80, a shaft 82, an adjustable retaining sleeve 84, and a surgical instrument retaining frame 86. The frame 86 has an open area 87 through which an instrument may be inserted. As illustrated in FIG. 21B, the shaft 82 includes a first threaded portion 88 that meshes with a second threaded portion 90 within the stabilizing arm 70'. The bottom of the shaft includes a disc 92 which is rotatably held in a slot 94 within the adjustable retaining sleeve 84. The sleeve 84 and disc 92 are free to rotate with respect to each other. The bottom exterior of the retaining sleeve 84 has a third threaded portion 96 that meshes with a fourth threaded portion 98 within the instrument retaining frame 84.

In use, the height of the retaining frame 86 is adjusted by turning knob 80. The intermeshing between the first and second threaded portions 88, 90 raises and lowers the entire shaft assembly comprising shaft 82 and sleeve 84. Because the retaining frame 86 is connected to the sleeve, 14, it is raised and lowered along with the shaft 82. However, because the disc 94 and sleeve 84 are free to rotate with respect to each other, the rotation of the knob is not translated to the third and fourth threaded portions 96, 98. A drill guide or other surgical instrument may be inserted into the opening 87 of the frame 86 and the adjustable sleeve 84 may be raised or lowered to snugly hold the drill guide in the frame 86. This is accomplished by rotating the sleeve 84. The rotation causes the intermeshing between the third and fourth threaded portions 96, 98 to raise and lower the bottom tip of the sleeve 94 within the open area 87. This permits the use of surgical instruments having a variety of diameters. Again, because the disc 94 and the sleeve 84 are free to rotate with respect to each other, the rotation of the sleeve 84 is not translated to the shaft 82.

Figure 22A:
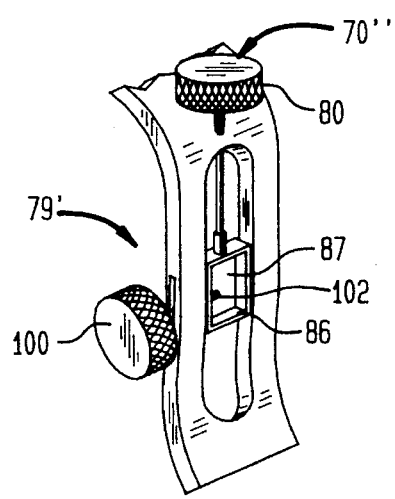
FIGS. 22A and 22B illustrate an alternative embodiment of the surgical instrument retaining screw of FIG. 21A and 21B.
Figure 22B:
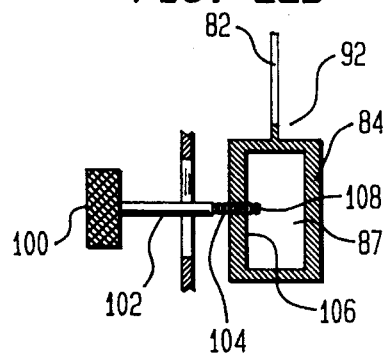

FIGS. 22A and 22B illustrate an alternative retaining screw mechanism 79'. This alternative mechanism has a knob 80 connected to a first shaft 82. The shaft is fixedly connected to the retaining frame 86. Turning knob 80 raises and lowers the retaining frame 86 as described above. A second knob 100 is connected to second shaft 102 which extends through the stabilizing arm 70' at a direction generally perpendicular to the first shaft 82. The second shaft 102 ends in a fifth threaded portion 104 which meshes with a sixth threaded portion 106 in a side of the retaining frame 86. Turning knob 100 moves a tip 108 of the second shaft 102 within the open area 87 to permit the use of a variety of different diameter surgical instruments.

The mandible retractor 50'''' illustrated in FIG. 20 also includes a suction fitting input 110 and a fiber optic input 112. The suction extends through the handle 52 via a channel 114 and down the retracting blade 54 through a tube 116 to supply suction at the surgical site. The suction tube 116 should be positioned to be out of the way of a bone plate mounted on shelf 64. An optical fiber 118 extends through the handle and down the retracting blade 54 to supply light to the surgical site.

Figure 23:
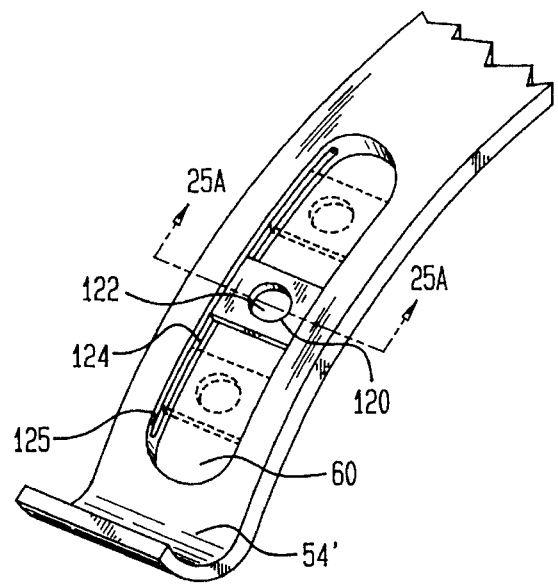
FIG. 23 illustrates a mandibular retractor having sliding drill sleeve according to one embodiment of the present invention.

FIGS. 23–26 illustrate two embodiments of a moveable surgical instrument guide, for a drill sleeve or other instrument. FIG. 23 illustrates a retractor blade 54' having an aperture 60. A guide 120, having a body 121 defining a hole 122, is slidably mounted in a groove 124 in the retractor blade side wall 125 defining the aperture 60. The guide 120 is shown in broken lines at other positions within the aperture 60.

Figure 24A:
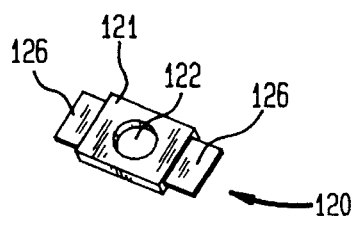
FIGS. 24A and 24B illustrate two alternative embodiments of sliding drill sleeves.
Figure 24B:
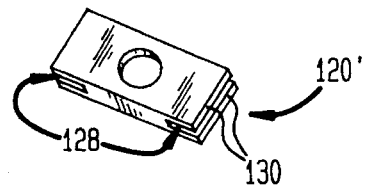

Two alternative guide configurations 120, 120' are illustrated in FIGS. 24A and 24B. FIG. 24A shows the moveable guide 120 of FIG. 23. The guide 120 comprises a body 121 defining a hole 122 and two side flanges 126 for extending into the grooves 124 in the retractor blade 54'. FIG. 23B shows a second configuration of moveable guide 120' for use with a retractor blade not having a groove. This guide 120 comprises sidewings 130 which extend from the top and bottom of the sides. These sidewings 130 define two channels 128. The channels 128 surround the retractor blade sidewalls 123, so that the sidewalls 123 extend through the channels 128.

Figure 25A:
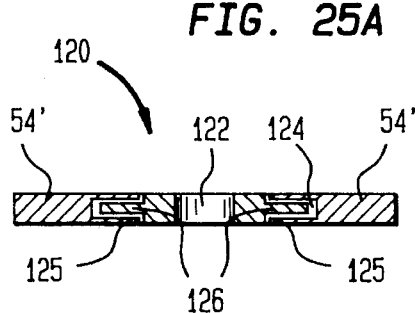
FIG. 25A is a cross sectional view of the retractor and sliding drill sleeve of FIG. 22, taken along line 25A—25A.
Figure 25B:
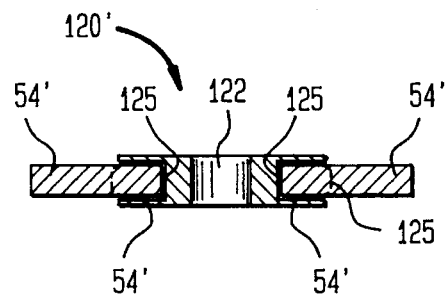
FIG. 25B is a cross sectional view of the sliding drill sleeve of FIG. 24B in place on a retractor.

The cooperation between the guides 120, 120' and the retractor blades 54, 54' are illustrated in FIGS. 25A and 25B. FIG. 25A is a cross sectional view of the retractor blade of FIG. 23. The guide side flanges 126 are within the grooves 124 in the sidewalls 125. FIG. 25B shows the wings 130 extending beyond the sidewalls to hold the guide 120' in position. Both configurations of the guide 120, 120' are maintained in a selected position by friction between the guide and the retractor blade.

Figure 26:
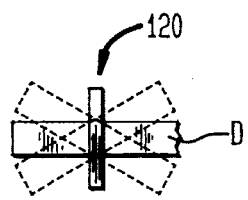
FIG. 26 is a side view of a sliding drill sleeve having a drill guide extending through it.

FIG. 26 illustrates a drill sleeve D inserted into a moveable guide 120. The hole 122 has a diameter slightly larger than the diameter of the drill sleeve D, thus allowing the drill sleeve to be manipulated to a variety of angles. The drill sleeve D is shown in several positions within the guide 110 in broken lines.

Figure 27A:
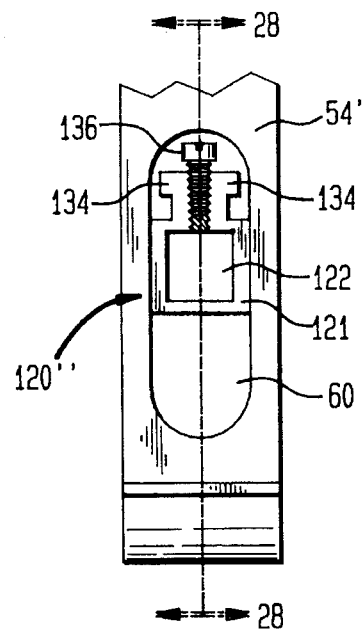
FIGS. 27A and 27B illustrate alternative embodiments of sliding drill sleeve guides.
Figure 27B:
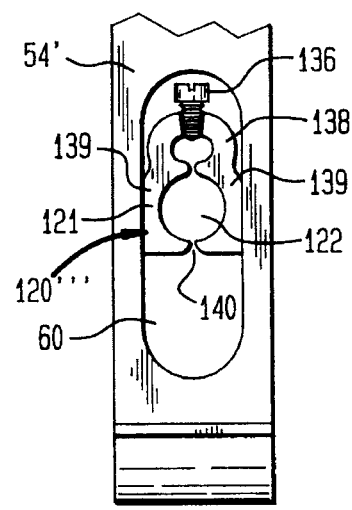
Figure 28:
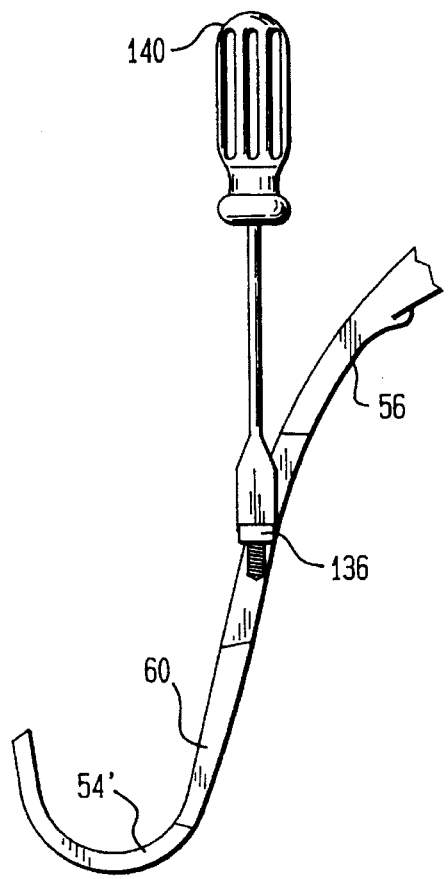
FIG. 28 is a cross sectional view of the drill sleeve guide of FIG. 27A and a screwdriver tightening a set screw.

FIGS. 27A, 27B, and 28 illustrate further alternative embodiments of the moveable guides. FIG. 27A shows a guide 120" having tabs 134 which expand outwardly when screw 136 is screwed down between the tabs 134. The tabs engage an inner wall of groove 124 (shown in FIG. 23) to hold the guide 120" in place. FIG. 27B shows a guide 120'" having curved tabs 138 which expand when screw 136 is screwed down between the tabs 138. The expansion of tabs 138 also causes the body 121 to rock about pivot points 139 causing a gap 140 in the bottom of the guide to narrow the hole 122, thus tightening around any instrument inserted into hole 122. FIG. 28 shows how screw 136 is tightened. A screwdriver 140 is inserted down into the aperture 60 to screw set screw 136. The curvilinear shape of the curved portion 56 allows easy access to the top of the screw 136.

Figure 29:
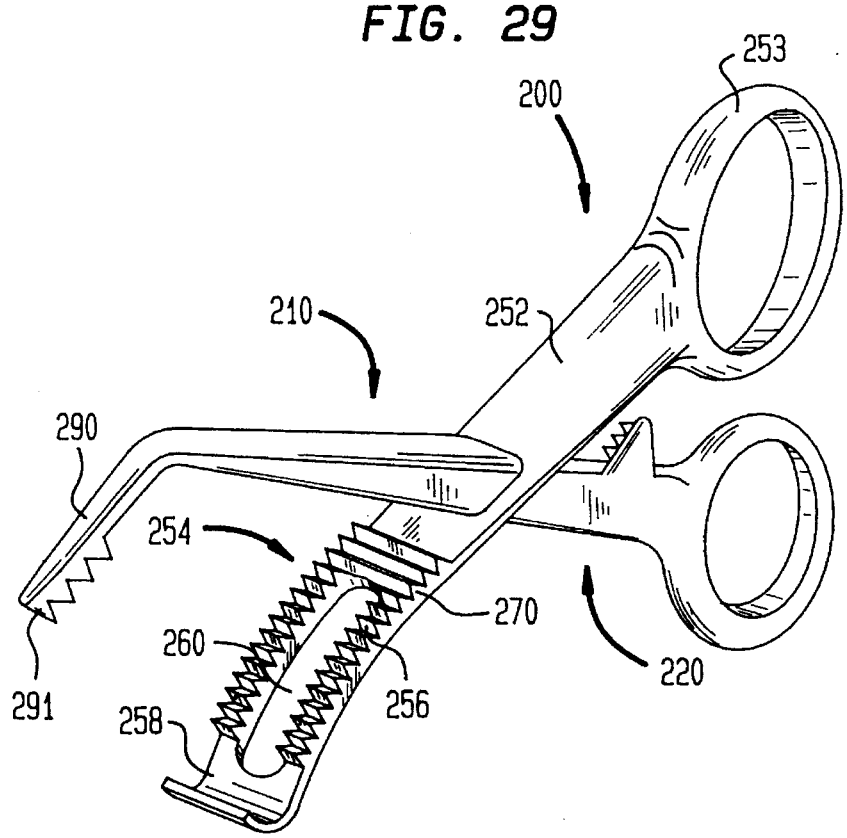
FIG. 29 is a perspective view of a retractor and clamp according to the present invention.
Figure 30:
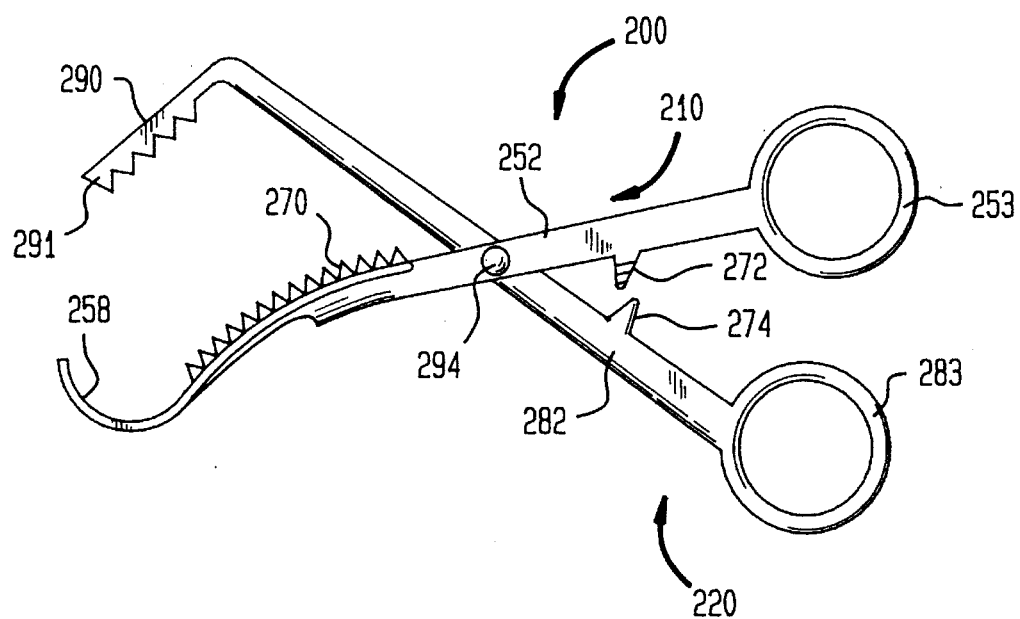
FIG. 30 is a side elevational view of the retractor and clamp of FIG. 29.
Figure 31:
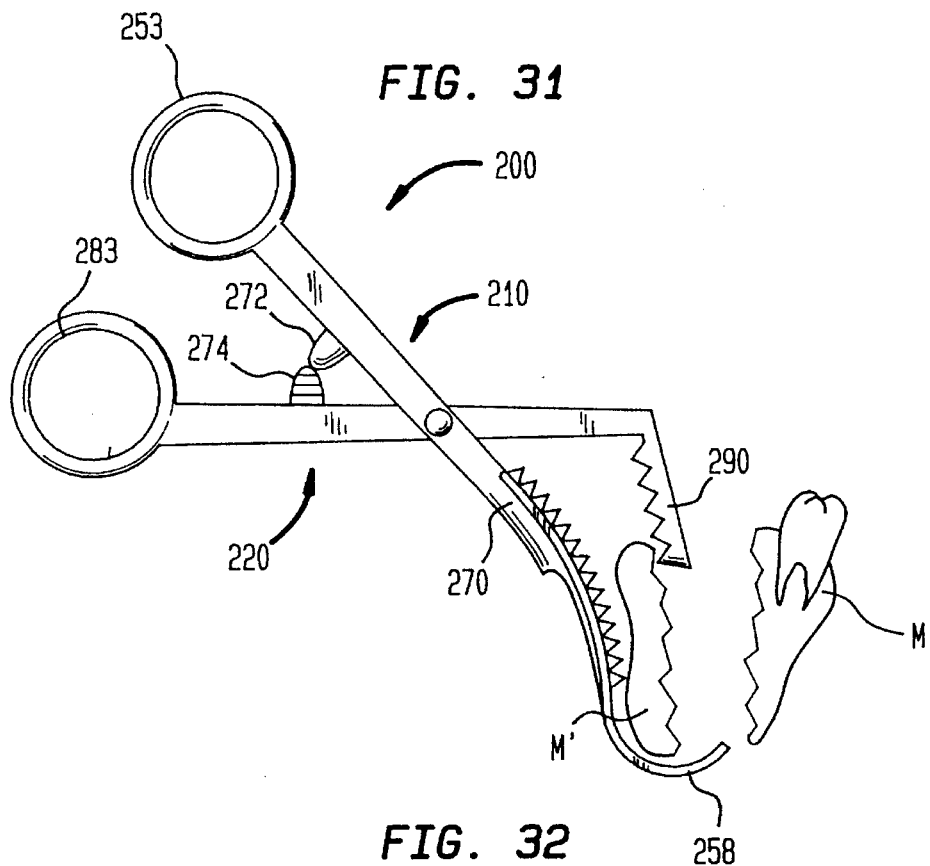
FIG. 31 is a side view of the retractor and clamp of FIG. 29 in use.

FIGS. 29–31 illustrate a clamp 200 according to the present invention. The clamp comprises a retractor arm 210 and a clamping arm 220. The retractor arm 210 comprises a handle 252 having a finger ring 253, and a retracting blade 254. The retracting blade 254 has a curved portion 256, an arcuate portion 258, and an aperture 260 defined by the retracting blade. The curved portion 256 and arcuate portions 258 have substantially the same shapes as described above in relation to FIGS. 4–9. The retracting arm 210 also has a first set of grasping teeth 270 located proximally of the aperture, and half of a standard hemostat ratchet 272. The clamping arm 220 has a handle 282 with a finger ring 283 and the other half of the hemostat ratchet 274. The distal end of clamping arm 220 is preferably angled with respect to the proximal end to provide better contact with the mandible, as illustrated in FIG. 31. Near the distal end of the clamping arm 220 is a beak 290 having a second set of clamping teeth 291. The beak may be made of stainless steel, nitinol, or tungsten carbide and may optionally be removable. The arms 210, 220 are pivotally connected by a swivel pin 294.

FIG. 31 illustrates the clamp 200 in use. The clamp 200 is particularly useful in removing broken pieces of mandible bone or during a sagittal ramis osteotomy. The arcuate portion 258 of the retracting arm 210 is positioned under and behind a broken piece M' of mandible M. The clamping arm 220 is swung into position by pulling up on ring 283 to cause the second set of clamping teeth 290 to contact a surface of the broken piece M'. The pressure of the teeth 290 pushes the broken piece against the first set of clamping teeth 270 on the retracting arm 210. The clamp may be held in place by locking the hemostat ratchet 272, 274. This provides the surgeon with a firm hold on the piece, which can now be easily removed or held in place to be fixated.

Figure 32:
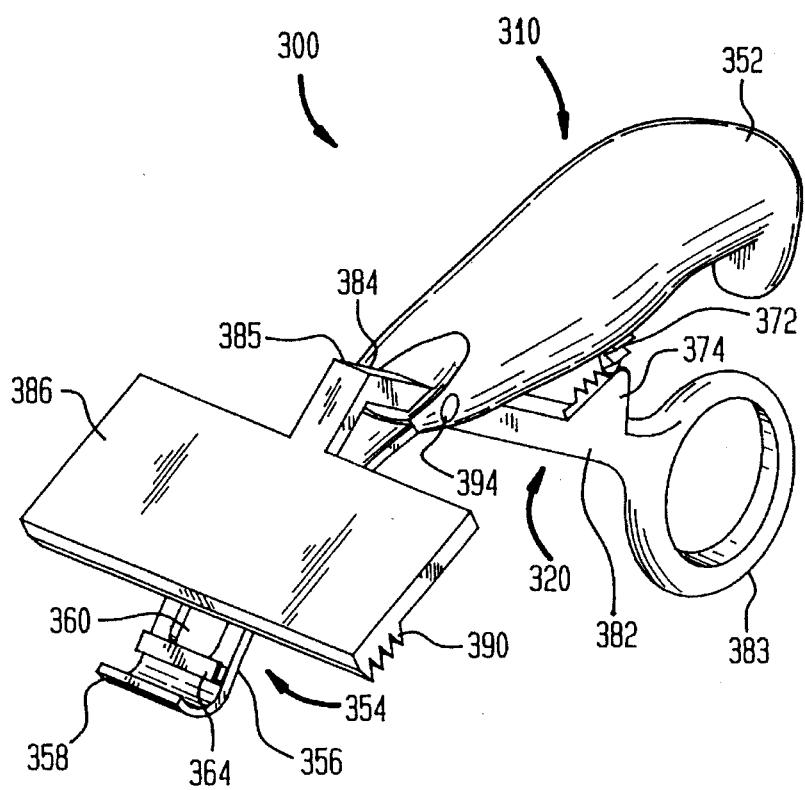
FIG. 32 is a perspective view of a retractor and reduction clamp according to the present invention.
Figure 33:
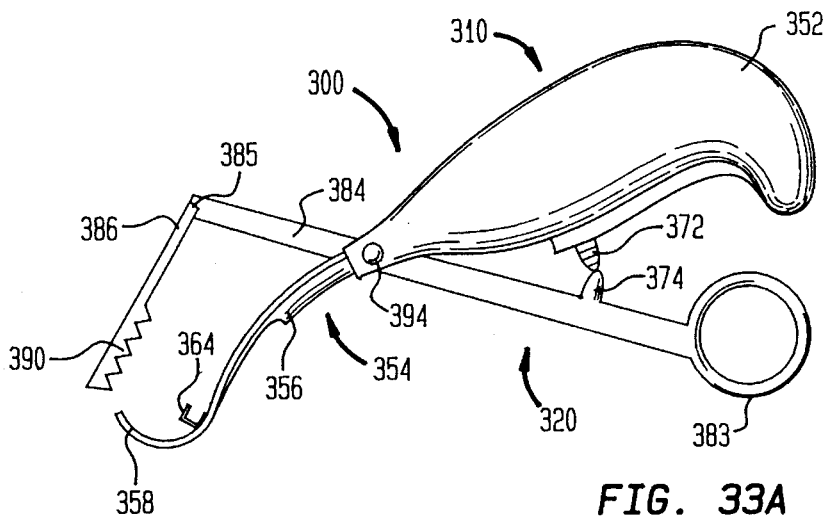
FIG. 33 is a side elevational view of the retractor and reduction clamp of FIG. 32.
Figure 34:
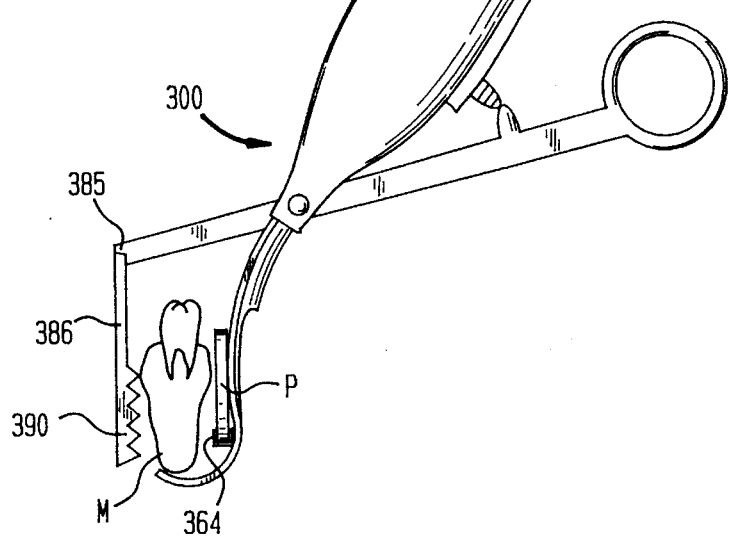
FIG. 34 is a side view of the retractor and reduction clamp of FIG. 32 in use.

FIGS. 32–34 illustrate a reducing clamp 300 according to the present invention. The reducing clamp 300 comprises a retractor 310 and a reducing clamp arm 320. The retractor is substantially the same as described with respect to FIGS. 4–9, or alternatively may have a shelf 364 for holding a bone plate. The retractor includes a handle 352 and a retracting blade 354. The retracting blade has a curved portion 354, an arcuate portion 358, and an aperture 360 defined in the retracting blade 354. The retractor may also have half of a standard hemostat ratchet 372. The reducing clamp arm 320 has a handle 382 with a finger ring 383 and the other half of the hemostat ratchet 374. The proximal end of the reducing clamp arm 320 has a straight portion 384 and a reducing plate 386 having a set of clamping teeth 390 facing the retracting blade 354. The second set of clamping teeth 390 may be sharp, as shown here, for direct contact with bone, or may be blunt, atraumatic teeth for contact with mucosa. The reducing plate 386 is preferably angled with respect to the straight portion 384. The reducing plate 386 may be narrow or broad. The preferred breadth depends on the nature of the fracture and bone structure. The reducing plate 386 may preferably be made of stainless steel, nitinol, or tungsten carbide and may optionally be removable. The angled joint 385 may be either permanently fixed or adjustably connected at various angles. The arms 310, 320 are pivotally connected by a swivel pin 394.

Figure 33A:
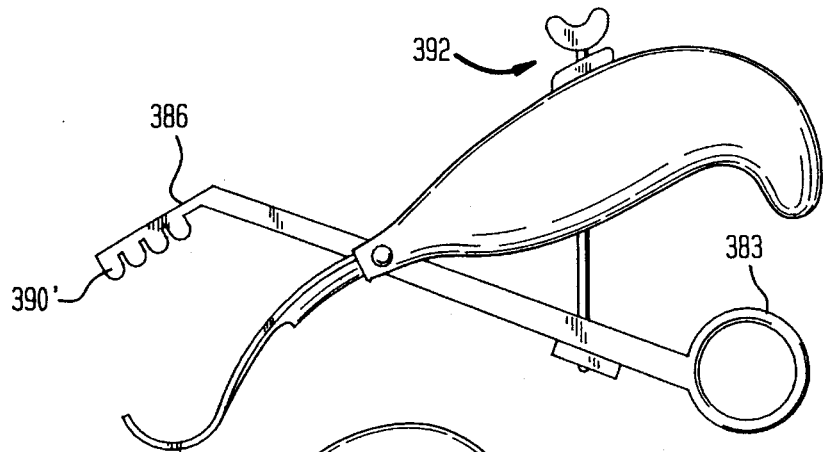
FIG. 33A is a side elevational view of the retractor and reduction clamp of FIG. 32.

FIG. 33A shows a reducing plate 386 having blunt, atraumatic teeth 390'. This embodiment also includes a wing nut mechanism 392 capable of retaining the clamping arm 320 in position without the surgeon continuously pulling up on finger ring 383.

FIG. 34 illustrates the reducing clamp 300 in use. The clamp 300 is particularly useful in reducing a fractured mandible. A bone plate P is inserted into the shelf 364. The arcuate portion 358 of the retracting arm 310 is positioned under and behind the mandible M. The reducing clamp arm 320 is swung into position by pulling up on ring 383 to cause the clamping teeth 390 to contact a posterior surface of the mandible M. The pressure of the teeth 390 pushes the mandible against the plate P. This presses the fractured mandible flat against the plate P by clamping the medial aspect of the incision. The reducing clamp 300 may also be used to hold a bone plate firmly in place. The clamp may be held in place by locking the hemostat ratchet 372, 374.

The mandibular retractors described herein are preferably made of stainless steel or other material suitable for surgical use.

While the invention has been described by the reference to specific embodiments, this was for purposes of illustration only and should not be construed to limit the spirit or the scope of the invention. For example, a person of ordinary skill in the art recognizes that the retractor according to the present invention may be used for procedures other than an ORIF and may be used on bones other than the mandible.

I claim:

1. A mandibular retractor, comprising:
   a. a handle; and
   b. a retractor blade connected to a distal end of the handle, the retractor blade including:
      (1) a curved portion at a proximal end of the retractor blade;
      (2) an arcuate portion having a tip, the arcuate portion connected to a distal end of the curved portion; and
      (3) an aperture defined in the retracting blade and located proximally from the tip, the aperture configured to allow a surgical instrument to extend through the retractor blade.

2. The mandibular retractor of claim 1, wherein the curved portion has a curvilinear shape defined to retract an oral incision parallel to a mandible in a direction generally perpendicularly away from the mandible when inserted into a patient's mouth.

3. The mandibular retractor of claim 1, wherein the curved portion has a curvilinear shape defined to retract a lateral aspect of a oral incision parallel to a mandible.

4. The mandibular retractor of claim 1, wherein the arcuate tip has a substantially semicircular shape.

5. The mandibular retractor of claim 1, further comprising a bone plate carrying shelf connected to the retractor blade distally of the aperture.

6. The mandibular retractor of claim 5, wherein the bone plate carrying shelf is shaped to snugly hold a bone plate.

7. The mandibular retractor of claim 1, wherein the retractor blade further comprises a side flange.

8. The mandibular retractor of claim 7, wherein the side flange tapers from a wide portion near a proximal end of the retractor blade to a narrow portion near a distal end of the retracting blade.

9. The mandibular retractor of claim 7, wherein the side flange is connected to a right side of the retractor blade.

10. The mandibular retractor of claim 7, wherein the side flange is connected to a left side of the retractor blade.

11. The mandibular retractor of claim 1, further comprising a stabilizing arm connected to the proximal end of the handle, including:
    a. an initial portion extending in a direction generally perpendicular a direction of the retracting blade;
    b. an central portion connected to a distal portion of the initial portion extending in a direction generally parallel to the curved portion;
    c. a curved tip curving in a direction opposite a curvature of the arcuate portion; and
    d. a stabilizing arm aperture defined in the central portion, the stabilizing arm aperture being generally aligned with the aperture defined by retracting blade.

12. The mandibular retractor of claim 11, wherein the central portion has a surface at a proximal end of the stabilizing arm aperture.

13. The mandibular retractor of claim 11, wherein the stabilizing arm further includes a surgical instrument retaining screw.

14. The mandibular retractor of claim 13, wherein the retaining screw includes:
    a. a knob;
    b. a shaft connected to the knob, the shaft extending at least partially through the central portion and having a first threaded portion intermeshed with second threaded portion in the central portion, and having an end opposite the knob;
    c. a sleeve rotatably fastened to the end of the shaft and having a third threaded portion at a tip opposite the end of the shaft; and
    d. a retaining frame defining an area through which a surgical instrument may be inserted and having a fourth threaded portion intermeshed with the third threaded portion.

15. The mandibular retractor of claim 12, wherein the retaining screw includes:
   a. a first knob;
   b. a first shaft connected to the first knob, the first shaft extending at least partially through the central portion and having a first threaded portion intermeshed with second threaded portion in the central portion, and having an end opposite the first knob;
   c. a second knob;
   d. a second shaft connected to the second knob, the second shaft extending at least partially through the central portion in a direction generally perpendicular to the first shaft, and having a third threaded portion, and having a tip opposite the second knob; and
   e. a retaining frame fixedly connected to the end of the first shaft, the frame defining an area through which a surgical instrument may be inserted and having a fourth threaded portion intermeshed with the third threaded portion.

16. The mandibular retractor of claim 1, further comprising a suction fitting input connectable to a channel which extends through the handle, and a tube connected to the channel which extends down the retractor blade.

17. The mandibular retractor of claim 1, further comprising a fiber optic input connectable to an optical fiber which extends through the handle and down the retractor blade.

18. The mandibular retractor of claim 1, further comprising a moveable surgical instrument guide having a body with a hole defined therein, the guide being located in the aperture defined in the curved portion.

19. The mandibular retractor of claim 18, wherein the retractor blade further includes a sidewall defining the aperture, the sidewall having a groove, and the guide having side flanges connected to the body, wherein the flanges are located in the groove.

20. The mandibular retractor of claim 18, wherein the retractor blade further includes sidewalls defining the aperture, and the guide further includes two sides and having side wings extending from a top and a bottom portion of both sides of the body defining a channel on each of the body, wherein the sidewalls extend through the channels.

21. The mandibular retractor of claim 18, wherein the hole defined in the guide body has a larger diameter than a surgical instrument to be inserted into the hole.

22. The mandibular retractor of claim 18, wherein the guide includes tabs, the tabs being expandably connected to a screw between the tabs.

23. The mandibular retractor of claim 22, wherein the guide body defines a gap pivotally connected to the screw for narrowing the hole when the screw is screwed down.

24. The mandibular retractor of claim 1, wherein the retractor further comprises a first set of clamping teeth located on the retracting blade distal from the aperture and further comprising a clamping arm pivotally connected to the retractor, the clamping arm having near a proximal end a second set of clamping teeth complementary to the first set of clamping teeth.

25. The mandibular retractor of claim 24, wherein the retractor handle includes a first finger ring at a distal end and the clamping arm includes a second finger ring at a distal end.

26. The mandibular retractor of claim 24, wherein the retractor handle and the clamping arm further include a hemostat ratchet.

27. The mandibular retractor of claim 1, wherein the retractor further comprises a reducing arm pivotally connected to the retractor, the reducing arm having a straight portion and a reducing plate connected to a proximal end of the straight portion, the reducing plate having a set of clamping teeth generally facing the retracting blade.

28. The mandibular retractor of claim 27, wherein the reducing arm includes a finger ring at a distal end.

29. The mandibular retractor of claim 27, wherein the retractor handle and the clamping arm further include a hemostat ratchet.

30. The mandibular retractor of claim 27, wherein the reducing plate is angled with respect to the straight portion.

31. The mandibular retractor of claim 27, wherein the reducing plate and the straight portion are adjustably connected.

32. A method for performing an open reduction and internal fixation of a fractured mandible, comprising the steps of:
   a. making an incision parallel to the mandible in a region of the fracture;
   b. inserting a retractor held in one hand into a mouth of the patient and locating a tip of the retractor behind the fractured mandible;
   c. aligning an aperture in the retractor between the incision and the fracture;
   d. using the retractor, retracting tissue laterally away from the fractured mandible and the fractured mandible may viewed by looking into the mouth;
   e. using the retractor, reducing the fractured mandible to its correct position;
   f. positioning across the fracture a bone plate defining at least one hole, the hole being aligned with the aperture in the retractor;
   g. while retracting the tissue with the retractor, using another hand to insert a drill through the incision, the aperture in the retractor, and the hole in the bone plate to drill at least one hole in the mandible aligned with the hole in the bone plate; and
   h. while retracting the tissue with the retractor, using the other hand to insert a screw and screw driver through the incision and the aperture in the retractor to screw a screw into the hole drilled in the mandible to hold the bone plate to the mandible.

33. The method of claim 32, further comprising loading the bone plate onto a shelf on the retractor before inserting the retractor into the patient's mouth.

34. The method of claim 32, further comprising the steps of:
   a. before the step of inserting the drill, aligning an aperture of a stabilizing arm with the incision; and
   b. the steps of inserting the drill and inserting the screwdriver further include inserting the drill and the screwdriver through the aperture in the stabilizing arm.

35. The method of claim 34, further comprising the step of adjusting a height of a surgical instrument retaining screw on the stabilizing arm before inserting the drill and screwdriver, respectively.

36. The method of claim 35, further comprising the step of positioning a tip in a surgical instrument retaining frame to accommodate a diameter of either one of the drill and the screwdriver.

37. The method of claim 32, further comprising the step of positioning a moveable surgical instrument guide in the aperture in the retractor before the step of inserting the drill.

38. The method of claim 32, wherein the step of making an incision includes making an incision in the patient's buccal vestibule.

39. The method of claim 38, wherein the step of making an incision includes making an incision in the patient's cutaneous region.

* * * * *